US011969296B2

(12) United States Patent
Noguchi

(10) Patent No.: US 11,969,296 B2
(45) Date of Patent: Apr. 30, 2024

(54) ULTRASOUND DIAGNOSTIC APPARATUS USING A HARMONIC IMAGING METHOD AND METHOD OF CONTROLLING ULTRASOUND DIAGNOSTIC APPARATUS

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/013,051

(22) Filed: Sep. 4, 2020

(65) Prior Publication Data

US 2020/0397412 A1 Dec. 24, 2020

Related U.S. Application Data

(63) Continuation of application No. PCT/JP2019/013237, filed on Mar. 27, 2019.

(30) Foreign Application Priority Data

Mar. 30, 2018 (JP) .................. 2018-067682

(51) Int. Cl.
*A61B 8/00* (2006.01)
*A61B 8/08* (2006.01)
(Continued)

(52) U.S. Cl.
CPC .................. *A61B 8/54* (2013.01); *A61B 8/14* (2013.01); *A61B 8/4488* (2013.01); *A61B 8/463* (2013.01);
(Continued)

(58) Field of Classification Search
CPC .................................................. G01S 7/52039
See application file for complete search history.

(56) References Cited

U.S. PATENT DOCUMENTS 6,506,158 B2 * 1/2003 Kawagishi .......... G01S 7/52026
600/443
6,537,222 B1 * 3/2003 Clark .................. G01S 7/52028
600/458
(Continued)

FOREIGN PATENT DOCUMENTS

EP 0770352 B1 * 12/2004 ............. A61B 8/463
JP 2001-258886 A 9/2001
(Continued)

OTHER PUBLICATIONS

JP-2017169984-A (Year: 2017).*
(Continued)

*Primary Examiner* — Joel Lamprecht
*Assistant Examiner* — Nyrobi Celestine
(74) *Attorney, Agent, or Firm* — Studebaker & Brackett PC

(57) ABSTRACT

An ultrasound diagnostic apparatus 1 includes a transducer array 2, a transmission unit 3 that transmits a set of a first ultrasonic pulse FP and a second ultrasonic pulse SP having phases inverted from each other on the same scanning line from the transducer array 2 into a subject N times to be equal to or greater than at least two times, a reception unit 4 that acquires reception signals from a signal output from the transducer array 2, which receives an ultrasound echo, a quadrature detection unit 5 that acquires an IQ signal string corresponding to the first ultrasonic pulse FP and an IQ signal string corresponding to the second ultrasonic pulse SP by performing quadrature detection in a determined range on the reception signals, and a bubble signal likelihood calculation unit 6 that calculates a bubble signal likelihood based on the IQ signal strings acquired by the quadrature detection unit 5.

6 Claims, 10 Drawing Sheets

(51) Int. Cl.
*A61B 8/14* (2006.01)
*G01N 29/24* (2006.01)
*G01N 29/44* (2006.01)

(52) U.S. Cl.
CPC ............ *A61B 8/481* (2013.01); *G01N 29/24* (2013.01); *G01N 29/44* (2013.01)

(56) References Cited

U.S. PATENT DOCUMENTS

| | | | |
|---|---|---|---|
| 6,726,630 B2* | 4/2004 | Kawagishi | A61B 8/481 600/458 |
| 9,743,909 B1 | 8/2017 | Sapozhnikov et al. | |
| 2001/0025143 A1 | 9/2001 | Suzuki | |
| 2002/0147398 A1 | 10/2002 | Kawagishi et al. | |
| 2003/0073903 A1 | 4/2003 | Sato | |
| 2003/0176792 A1 | 9/2003 | Kawagishi et al. | |
| 2005/0059893 A1* | 3/2005 | Ogasawara | A61B 8/461 600/437 |
| 2005/0256404 A1* | 11/2005 | Sato | A61B 8/481 600/437 |
| 2008/0221449 A1* | 9/2008 | Sato | G01S 15/8988 600/442 |
| 2008/0275338 A1 | 11/2008 | Jensen et al. | |
| 2008/0294049 A1 | 11/2008 | Guracar | |
| 2010/0056924 A1* | 3/2010 | Powers | A61B 8/481 600/458 |
| 2010/0081857 A1* | 4/2010 | Georgi | A61K 51/1045 600/1 |
| 2010/0298709 A1* | 11/2010 | Needles | A61B 8/06 600/458 |
| 2016/0066888 A1 | 3/2016 | Yao et al. | |
| 2016/0331346 A1 | 11/2016 | Bruce et al. | |
| 2016/0343134 A1* | 11/2016 | Averkiou | G06F 18/22 |
| 2016/0363527 A1* | 12/2016 | Ruan | A61B 5/00 |
| 2017/0164923 A1* | 6/2017 | Matsumoto | A61B 5/026 |
| 2018/0330518 A1* | 11/2018 | Choi | A61B 8/42 |
| 2019/0154822 A1* | 5/2019 | Berlin | G06T 5/50 |
| 2021/0000448 A1* | 1/2021 | Rychak | A61K 49/221 |

FOREIGN PATENT DOCUMENTS

| | | | |
|---|---|---|---|
| JP | 2002-301068 A | | 10/2002 |
| JP | 2003-230559 A | | 8/2003 |
| JP | 2006-326178 A | | 12/2006 |
| JP | 2014-171755 A | | 9/2014 |
| JP | 2017169984 A | * | 9/2017 |
| WO | 2010/121265 A1 | | 10/2010 |

OTHER PUBLICATIONS

N. F. Haq et al., "A data-driven approach to prostate cancer detection from dynamic contrast enhanced MRI", Computerized Medical Imaging and Graphics, vol. 41, pp. 37-45, Jun. 2014 (Year: 2014).*

Z. Akkus, "Image Analysis for Contrast Enhanced Ultrasound Carotid Plaque Imaging", Thesis, pp. 1-204, 2014 (Year: 2014).*

A. Postema et al., "Ultrasound modalities and quantification: developments of multiparametric ultrasonography, a new modality to detect, localize and target prostatic tumors", Current Opinion in Urology, vol. 25, No. 3, pp. 191-197, Jan. 2015 (Year: 2015).*

J. Ilonen et al, "Comparison of bubble detectors and size distribution estimators", Pattern Recognition Letters, vol. 101, pp. 60-66, Nov. 2017 (Year: 2017).*

International Search Report issued in PCT/JP2019/013237; dated May 28, 2019.

Written Opinion issued in PCT/JP2019/013237; dated May 28, 2019.

Monica Siepmann et al.; "Phase shift variance imaging for contrast agent detection"; Ultrasonics Symposium (IUS); 2010 IEEE; Oct. 11, 2010; pp. 1944-1947; IEEE; XP031952799; ISBN: 978-1-4577-0382-9.

The extended European search report issued by the European Patent Office dated Apr. 23, 2021, which corresponds to European Patent Application No. 19774254.7-1126 and is related to U.S. Appl. No. 17/013,051.

* cited by examiner

ULTRASOUND DIAGNOSTIC APPARATUS USING A HARMONIC IMAGING METHOD AND METHOD OF CONTROLLING ULTRASOUND DIAGNOSTIC APPARATUS

CROSS-REFERENCE TO RELATED APPLICATIONS

This application is a Continuation of PCT International Application No. PCT/JP2019/013237 filed on Mar. 27, 2019, which claims priority under 35 U.S.C. § 119(a) to Japanese Patent Application No. 2018-067682 filed on Mar. 30, 2018. The above application is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and in particular, to an ultrasound diagnostic apparatus and a method of controlling an ultrasound diagnostic apparatus that generate an ultrasound image using a harmonic imaging method.

2. Description of the Related Art

In a medical ultrasound diagnostic apparatus, in a case where a contrast medium is introduced into a subject to perform diagnosis, or the like, as disclosed in JP2002-301068A and JP2003-230559A, there is known a so-called harmonic imaging method that uses nonlinearity of the contrast medium, and extracts and images a nonlinear component from an ultrasound echo received by a transducer array. With the use of the harmonic imaging method, an image having high contrast in a tissue of the subject and bubbles of the contrast medium can be generated.

In the harmonic imaging method, as a method of extracting the nonlinear component from the ultrasound echo, for example, there is known a pulse inversion method that sequentially transmits a first ultrasonic pulse and a second ultrasonic pulse having phases inverted from each other on the same scanning line, and adds a reception signal of the first ultrasonic pulse and a reception signal of the second ultrasonic pulse. With the pulse inversion method, it is possible to eliminate a fundamental signal having a range of a fundamental wave forming the first ultrasonic pulse and the second ultrasonic pulse from the reception signals based on the ultrasound echo to extract a nonlinear signal due to the bubbles of the contrast medium.

SUMMARY OF THE INVENTION

However, normally, even though the pulse inversion method is used, a signal due to an ultrasound echo from a boundary or the like of the tissue often remains to the same extent as the nonlinear signal due to the bubbles of the contrast medium, and there is a problem in that it is hard to distinguish between the signal and the nonlinear signal. In the related art, in many cases, a temporal change in luminance of a signal with movement of the bubbles of the contrast medium within a blood vessel is observed to distinguish between the signal due to the ultrasound echo from the boundary or the like of the tissue and the nonlinear signal due to the bubbles of the contrast medium, and a time is needed to determine which signal of the acquired signals is the nonlinear signal due to the bubbles of the contrast medium.

In a case where there is the motion of the tissue, such as pulsation, in the subject, the fundamental signal that remains without being cancelled by the pulse inversion method increases, and there is a problem in that it is hard to distinguish between the fundamental signal and the nonlinear signal due to the bubbles of the contrast medium.

The invention has been accomplished in order to solve such a problem in the related art, and an object of the invention is to provide an ultrasound diagnostic apparatus and a method of controlling an ultrasound diagnostic apparatus capable of distinguishing between a signal due to a tissue of a subject and a signal due to bubbles of a contrast medium easily and in a short time.

In order to achieve the above-described object, the invention provides an ultrasound diagnostic apparatus comprising a transducer array, a transmission unit that transmits a set of a first ultrasonic pulse and a second ultrasonic pulse having phases inverted from each other on the same scanning line from the transducer array into a subject N times equal to or greater than at least two times, a reception unit that acquires reception signals based on a signal output from the transducer array, which receives an ultrasound echo generated in the subject, a quadrature detection unit that acquires an IQ signal string corresponding to the first ultrasonic pulse and an IQ signal string corresponding to the second ultrasonic pulse by performing quadrature detection in a determined range on the reception signals acquired by the reception, a pulse inversion addition unit that acquires image signals with a fundamental component eliminated by adding IQ signals corresponding to the first ultrasonic pulse and IQ signals corresponding to the second ultrasonic pulse using the IQ signal strings acquired by the quadrature detection unit, a bubble signal likelihood calculation unit that calculates a bubble signal likelihood based on the IQ signal strings acquired by the quadrature detection unit, and an image generation unit that generates an ultrasound image based on the bubble signal likelihood calculated by the bubble signal likelihood calculation unit and the image signals acquired by the pulse inversion addition unit.

The bubble signal likelihood calculation unit may obtain autocorrelation from the IQ signal strings acquired by the quadrature detection unit and may calculate the bubble signal likelihood based on the obtained autocorrelation.

Alternatively, the bubble signal likelihood calculation unit may calculate a variance value of a phase difference from the IQ signal strings acquired by the quadrature detection unit and may calculate the bubble signal likelihood using the calculated variance value of the phase difference.

Alternatively, the bubble signal likelihood calculation unit may calculate a variance value of amplitude from the IQ signal strings acquired by the quadrature detection unit and may calculate the bubble signal likelihood using the calculated variance value of the amplitude.

The ultrasound diagnostic apparatus may further comprise a nonlinear signal information calculation unit that calculates at least one of power or a velocity of a nonlinear signal from the image signals acquired by the pulse inversion addition unit.

In this case, the image generation unit may generate the ultrasound image based on at least one of the power or the velocity of the nonlinear signal calculated by the nonlinear signal information calculation unit.

The image generation unit may generate the ultrasound image according to a color map based on at least one of the power or the velocity of the nonlinear signal calculated by the nonlinear signal information calculation unit and the bubble signal likelihood calculated by the bubble signal likelihood calculation unit.

The ultrasound diagnostic apparatus may further comprise a display unit that displays the ultrasound image.

The invention provides a method of controlling an ultrasound diagnostic apparatus comprising transmitting a set of a first ultrasonic pulse and a second ultrasonic pulse having phases inverted from each other on the same scanning line from the transducer array into a subject N times equal to or greater than at least two times, acquiring reception signals based on a signal output from the transducer array, which receives an ultrasound echo generated in the subject, acquiring an IQ signal string corresponding to the first ultrasonic pulse and an IQ signal string corresponding to the second ultrasonic pulse by performing quadrature detection in a determined range on the acquired reception signals, acquiring image signals with a fundamental component eliminated by adding IQ signals corresponding to the first ultrasonic pulse and IQ signals corresponding to the second ultrasonic pulse using the acquired IQ signal strings, calculating a bubble signal likelihood based on the acquired IQ signal strings, and generating an ultrasound image based on the calculated bubble signal likelihood and the acquired image signals.

According to the invention, since the bubble signal likelihood calculation unit that calculates an index representing the randomness of the IQ signal strings acquired by the quadrature detection unit as the bubble signal likelihood is provided, it is possible to distinguish a signal due to a tissue of the subject and a signal due to bubbles of a contrast medium easily and in a short time.

DESCRIPTION OF THE PREFERRED EMBODIMENTS

Hereinafter, embodiments of the invention will be described referring to the accompanying drawings. In the following description, it is assumed that a contrast medium is introduced into a subject.

Embodiment

Figure 1:
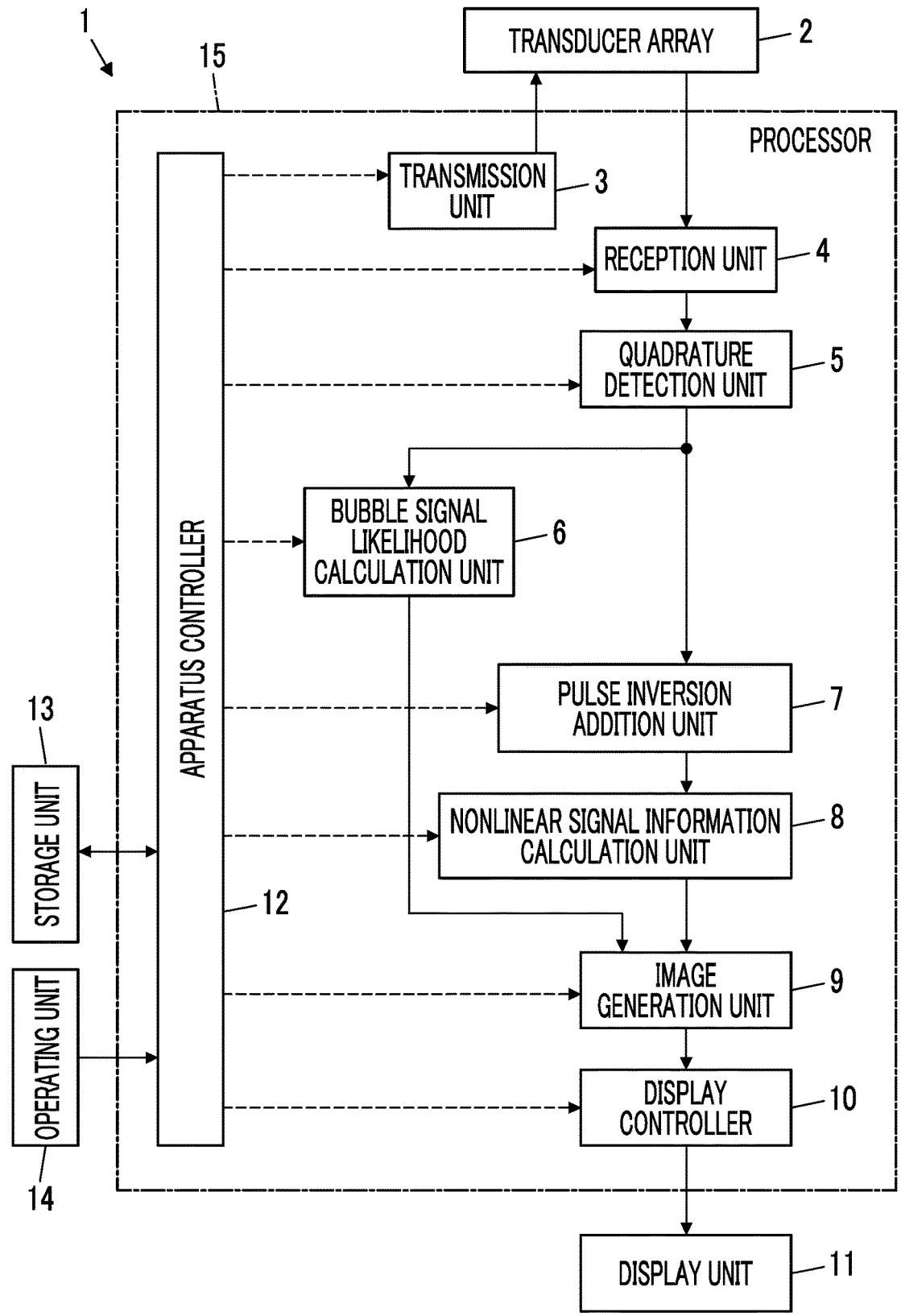
FIG. 1 is a block diagram showing the configuration of an ultrasound diagnostic apparatus according to an embodiment of the invention.

FIG. 1 shows the configuration of an ultrasound diagnostic apparatus 1 according to an embodiment of the invention. As shown in FIG. 1, the ultrasound diagnostic apparatus 1 comprises a transducer array 2, and a transmission unit 3 and a reception unit 4 are connected to the transducer array 2. A quadrature detection unit 5 is connected to the reception unit 4, and a bubble signal likelihood calculation unit 6 and a pulse inversion addition unit 7 are connected to the quadrature detection unit 5. A nonlinear signal information calculation unit 8, an image generation unit 9, a display controller 10, and a display unit 11 are sequentially connected to the pulse inversion addition unit 7. The bubble signal likelihood calculation unit 6 is connected to the image generation unit 9.

An apparatus controller 12 is connected to the transmission unit 3, the reception unit 4, the quadrature detection unit 5, the bubble signal likelihood calculation unit 6, the pulse inversion addition unit 7, the nonlinear signal information calculation unit 8, the image generation unit 9, and the display controller 10, and a storage unit 13 and an operating unit 14 are connected to the apparatus controller 12. The apparatus controller 12 and the storage unit 13 are connected to perform bidirectional transfer of information to each other.

The transmission unit 3, the reception unit 4, the quadrature detection unit 5, the bubble signal likelihood calculation unit 6, the pulse inversion addition unit 7, the nonlinear signal information calculation unit 8, the image generation unit 9, the display controller 10, and the apparatus controller 12 constitute a processor 15.

The transducer array 2 of the ultrasound diagnostic apparatus 1 shown in FIG. 1 has a plurality of transducers arranged in a one-dimensional or two-dimensional manner. Each transducer transmits an ultrasonic wave in response to an actuation signal supplied from the transmission unit 3, receives an ultrasound echo from a subject, and outputs a signal based on the ultrasound echo. Each transducer is constituted by forming electrodes at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the processor 15 includes, for example, a plurality of pulse generators, and adjusts a delay amount of each drive voltage based on a transmission delay pattern selected according to a control signal from the apparatus controller 12 such that the ultrasonic waves transmitted from a plurality of transducers of the transducer array 2 form ultrasonic beam, and supplies the drive voltages to a plurality of transducers. In this way, in a case where the pulsed drive voltage is applied to the electrodes of each of a plurality of transducers of the transducer array 2, the piezoelectric body expands and contracts to generate a pulsed ultrasonic wave from the transducer, and a pulsed ultrasonic beam, that is, an ultrasonic pulse is formed from a combined wave of the ultrasonic waves. The transmission unit 3 sequentially generates a first ultrasonic pulse and a second ultrasonic pulse having phases inverted from each other from the transducer array 2 in this manner, and transmits a set of the first ultrasonic pulse and the second ultrasonic pulse into the subject along the same scanning line through the transducer array 2 multiple times.

The first ultrasonic pulse and the second ultrasonic pulse transmitted into the subject are reflected, for example, from a target, such as a part of the subject, and propagate through the subject toward the transducer array 2 as a so-called ultrasound echo. The ultrasound echo propagating toward the transducer array 2 is received by each transducer constituting the transducer array 2. In this case, each transducer constituting the transducer array 2 expands and contracts with reception of the propagating ultrasound echo to generate an electrical signal, and output the electrical signal to the reception unit 4.

Figure 2:
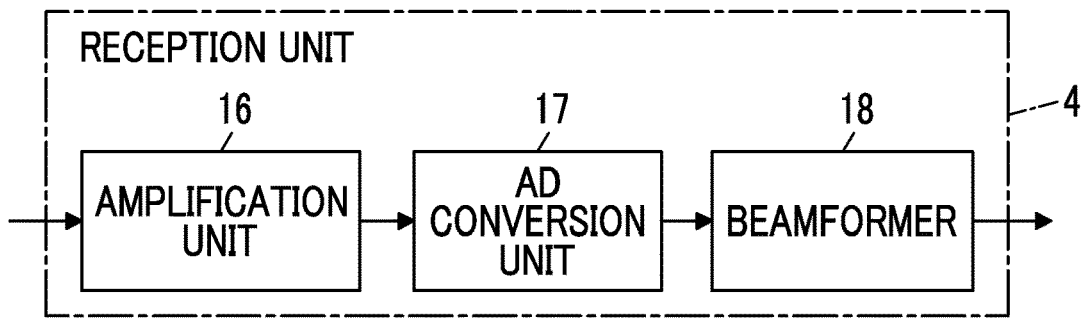
FIG. 2 is a block diagram showing the internal configuration of a reception unit in the embodiment of the invention.

The reception unit 4 of the processor 15 executes processing of the signals output from the transducer array 2 in response to a control signal from the apparatus controller 12. As shown in FIG. 2, the reception unit 4 has a configuration in which an amplification unit 16, an analog-digital (AD) conversion unit 17, and a beamformer 18 are connected in series.

The amplification unit 16 of the reception unit 4 amplifies the signal input from each transducer constituting the transducer array 2 and transmits the amplified signal to the AD conversion unit 17. The AD conversion unit 17 converts the signal transmitted from the amplification unit 16 into digital data and transmits the converted data to the beamformer 18. The beamformer 18 executes so-called reception focus processing in which a delay is given to each piece of data converted by the AD conversion unit 17 in compliance with a sound speed or a distribution of a sound speed based on a reception delay pattern selected according to a control signal from the apparatus controller 12 and addition is performed. With the reception focus processing, each piece of data converted by the AD conversion unit 17 is subjected to phasing addition, and a reception signal with a narrowed focus of the ultrasound echo is acquired.

Figure 3:
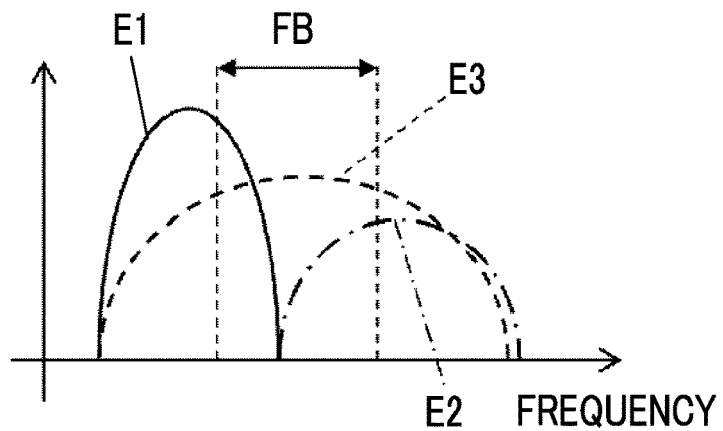
FIG. 3 is a diagram showing an example of a range of quadrature detection corresponding to a first ultrasonic pulse.
Figure 4:
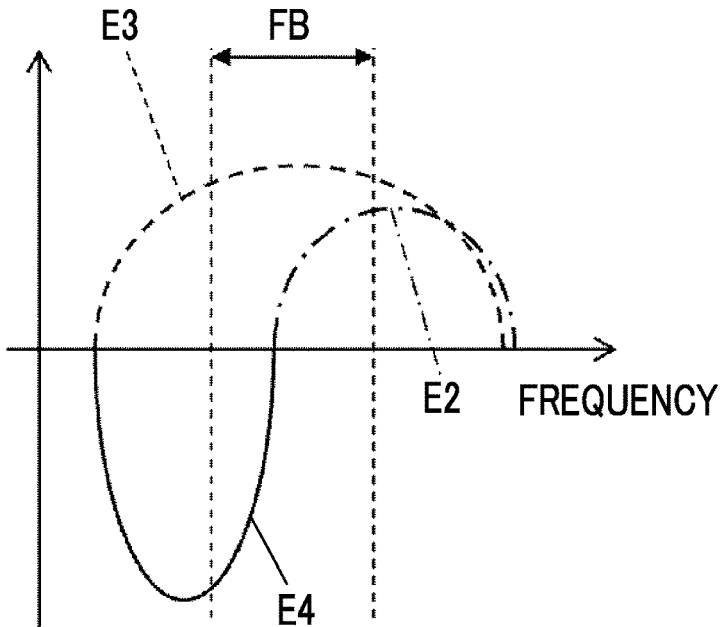
FIG. 4 is a diagram showing an example of a range of quadrature detection corresponding to a second ultrasonic pulse.

Here, the ultrasound echo propagating through the subject includes a fundamental component having a range of a fundamental wave forming the first ultrasonic pulse and the second ultrasonic pulse, a secondary harmonic component due to motion of a tissue of the subject, and a nonlinear component due to micro vibration of bubbles of the contrast medium introduced into the subject. For this reason, for example, as shown in FIGS. 3 and 4, the reception signals acquired by the reception unit 4 include a fundamental signal E1 or E4 based on the fundamental component of the ultrasound echo, a secondary harmonic signal E2 based on the secondary harmonic component, and a bubble signal E3 based on the nonlinear component resulting from the bubbles of the contrast medium. In the example shown in FIG. 3, a reception signal based on an ultrasonic pulse having a positive phase is shown, and the fundamental signal E1 has a positive value. On the other hand, in the example shown in FIG. 4, a reception signal based on an ultrasonic pulse having a negative phase is shown, and the fundamental signal E4 has a negative value.

The quadrature detection unit 5 of the processor 15 performs quadrature detection on the reception signals to convert the reception signals into IQ signals to be complex data by mixing a carrier signal having a reference frequency with the reception signals acquired by the reception unit 4 and acquires an IQ signal string corresponding to the first ultrasonic pulse and an IQ signal string corresponding to the second ultrasonic pulse. In this case, in order to improve the detection accuracy of the contrast medium introduced into the subject, as shown in FIGS. 3 and 4, it is desirable that the quadrature detection unit 5 compares the signal intensity of the fundamental signal E1 with the signal intensity of the secondary harmonic signal E2 and sets the range FB of quadrature detection so as to include a frequency at which the signal intensity of the bubble signal E3 having a nonlinear signal due to the bubbles of the contrast medium becomes relatively large. As shown in FIGS. 3 and 4, it is preferable that the range FB of quadrature detection is set so as to include a part of a frequency range of the fundamental signal E1 or E4 in addition to a frequency at which the bubble signal E3 becomes relatively large such that the signal intensity of the fundamental signal E1 and the signal intensity of a nonlinear signal including the secondary harmonic signal E2 and the bubble signal E3 have values comparatively close to each other.

The bubble signal likelihood calculation unit 6 of the processor 15 calculates an index using autocorrelation or a variance value calculated based on the IQ signal strings acquired by the quadrature detection unit 5 as a bubble signal likelihood based on the bubbles of the contrast medium introduced into the subject. The calculation of the bubble signal likelihood in the bubble signal likelihood calculation unit 6 will be described below in detail.

The pulse inversion addition unit 7 of the processor 15 adds the IQ signals corresponding to the first ultrasonic pulse and the IQ signals corresponding to the second ultrasonic pulse using the IQ signal strings acquired by the quadrature detection unit 5, thereby acquiring added signals having the fundamental signals E1 and E4 shown in FIGS. 3 and 4 eliminated.

The nonlinear signal information calculation unit 8 of the processor 15 calculates, as nonlinear signal information, at least one of power or a velocity of the nonlinear signal including the secondary harmonic signal E2 due to the tissue of the subject and the bubble signal E3 due to the bubbles of the contrast medium introduced into the subject from the added signals acquired by the pulse inversion addition unit 7.

The image generation unit 9 of the processor 15 generates an ultrasound image based on at least one of the power or the velocity of the nonlinear signal calculated by the nonlinear signal information calculation unit 8 and the bubble signal likelihood calculated by the bubble signal likelihood calculation unit 6.

The display controller 10 of the processor 15 executes predetermined processing on the ultrasound image and the like and makes the display unit 11 display the ultrasound image and the like generated by the image generation unit 9 under the control of the apparatus controller 12.

The display unit 11 of the ultrasound diagnostic apparatus 1 displays an image and the like under the control of the display controller 10, and includes, for example, a display device, such as a liquid crystal display (LCD).

The operating unit 14 of the ultrasound diagnostic apparatus 1 is provided for the user performing an input operation, and can comprise a keyboard, a mouse, a trackball, a touch pad, a touch panel, and the like.

The storage unit 13 stores an operation program and the like of the ultrasound diagnostic apparatus 1, and a recording medium, such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The processor 15 having the transmission unit 3, the reception unit 4, the quadrature detection unit 5, the bubble signal likelihood calculation unit 6, the pulse inversion addition unit 7, the nonlinear signal information calculation unit 8, the image generation unit 9, the display controller 10, and the apparatus controller 12 is constituted of a central processing unit (CPU) and a control program causing the CPU to execute various kinds of processing; however, the processor 15 may be constituted using a field programmable gate array (FPGA), a digital signal processor (DSP), an application specific integrated circuit (ASIC), a graphics processing unit (GPU), and other integrated circuits (ICs). The transmission unit 3, the reception unit 4, the quadrature detection unit 5, the bubble signal likelihood calculation unit 6, the pulse inversion addition unit 7, the nonlinear signal information calculation unit 8, the image generation unit 9, the display controller 10, and the apparatus controller 12 may be incorporated partially or entirely in one CPU or the like.

Figure 5:
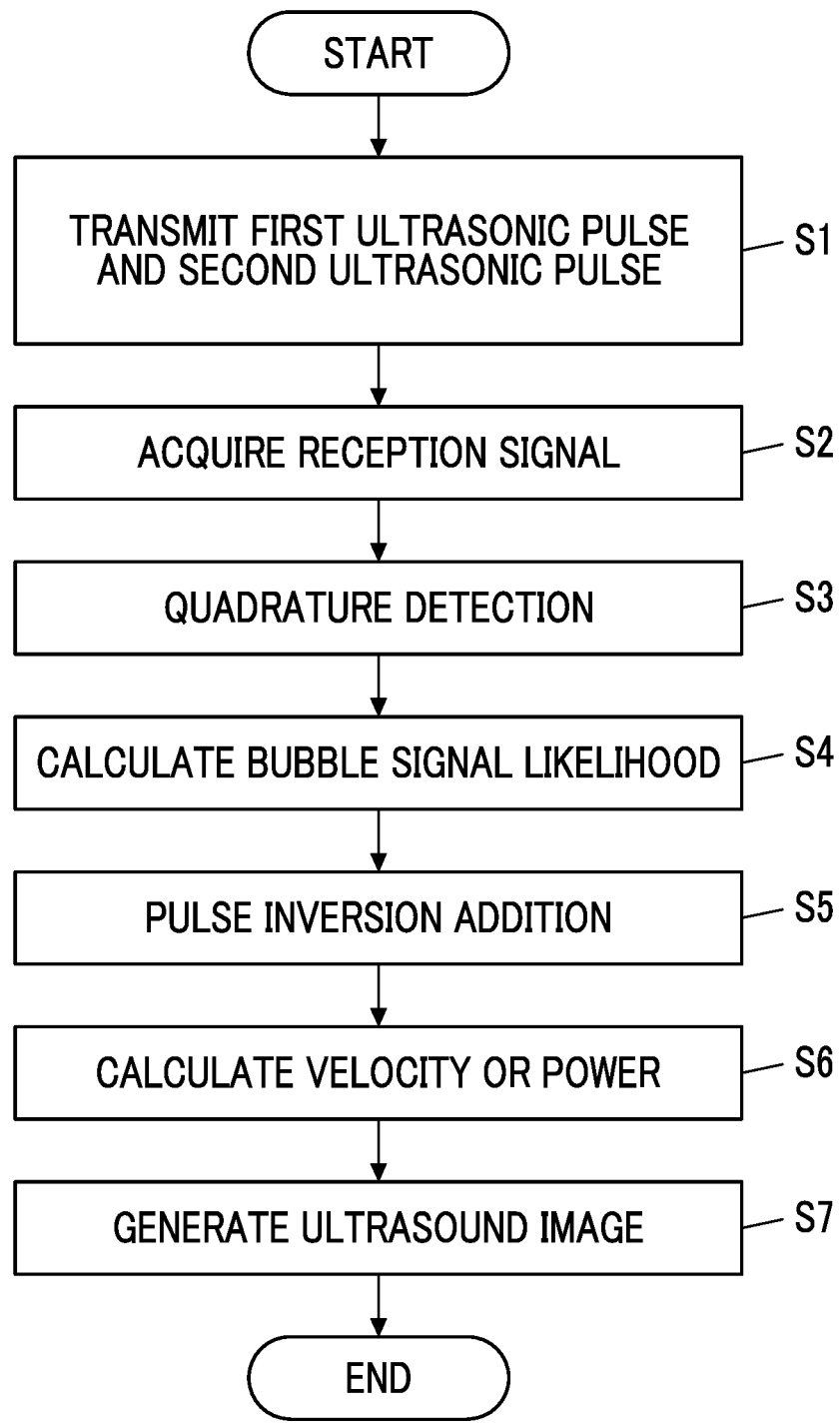
FIG. 5 is a flowchart representing the operation of the ultrasound diagnostic apparatus according to the embodiment of the invention.

Next, the operation of the ultrasound diagnostic apparatus 1 in the embodiment will be described in detail referring to a flowchart of FIG. 5. In the embodiment, the ultrasound diagnostic apparatus 1 sequentially transmits the first ultrasonic pulse and the second ultrasonic pulse having phases inverted from each other on the same scanning line and generates the ultrasound image using a pulse inversion method that adds a reception signal of the first ultrasonic pulse and a reception signal of the second ultrasonic pulse.

Figure 6:
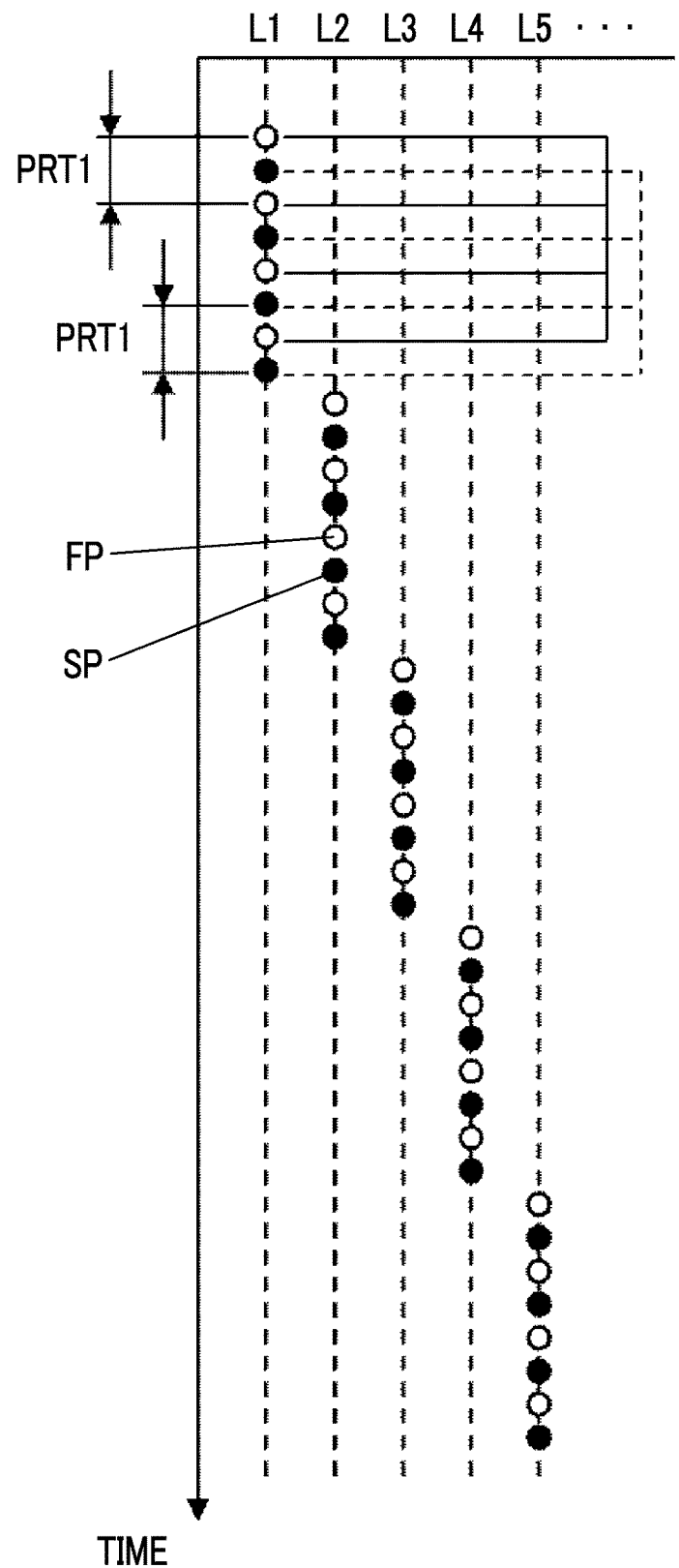
FIG. 6 is a diagram schematically showing a transmission timing of an ultrasonic pulse.

First, in Step S1, the transmission unit 3 transmits the first ultrasonic pulse and the second ultrasonic pulse having phases inverted from each other on the same scanning line multiple times through the transducer array 2. In this case, the transmission unit 3 transmits a set of the first ultrasonic pulse and the second ultrasonic pulse on the same scanning line N times, and then, transmits a set of the first ultrasonic pulse and the second ultrasonic pulse on the next scanning line N times. Here, N is an integer equal to or greater than two. For example, as shown in FIG. 6, the transmission unit 3 alternately transmits a first ultrasonic pulse FP and a second ultrasonic pulse SP on each of scanning lines L1, L2, L3, L4, and L5 four times. In the example shown in FIG. 6, a time interval PRT1 between the first ultrasonic pulses FP adjacent in time series and a time interval PRT1 between the second ultrasonic pulses SP adjacent in time series are equal to each other.

In Step S2, the reception unit 4 acquires the reception signals based on the signal output from the transducer array 2 received the ultrasound echo generated in the subject based on the first ultrasonic pulse FP and the second ultrasonic pulse SP transmitted into the subject in Step S1.

Subsequently, in Step S3, the quadrature detection unit 5 performs quadrature detection in the range FB determined for the reception signals acquired in Step S2, thereby acquiring the IQ signal string corresponding to the first ultrasonic pulse FP and the IQ signal string corresponding to the second ultrasonic pulse. In this case, for example, as shown in FIGS. 3 and 4, the quadrature detection unit 5 compares the signal intensity of the fundamental signal E1 with the signal intensity of the secondary harmonic signal E2, sets range FB of quadrature detection such that the signal intensity of the bubble signal E3 having the nonlinear signal due to the bubbles of the contrast medium becomes relatively large, and the signal intensity of the fundamental signal E1 and the signal intensity of the nonlinear signal including the secondary harmonic signal E2 and the bubble signal E3 have values close to each other, and executes quadrature detection in the range FB.

Figure 7:
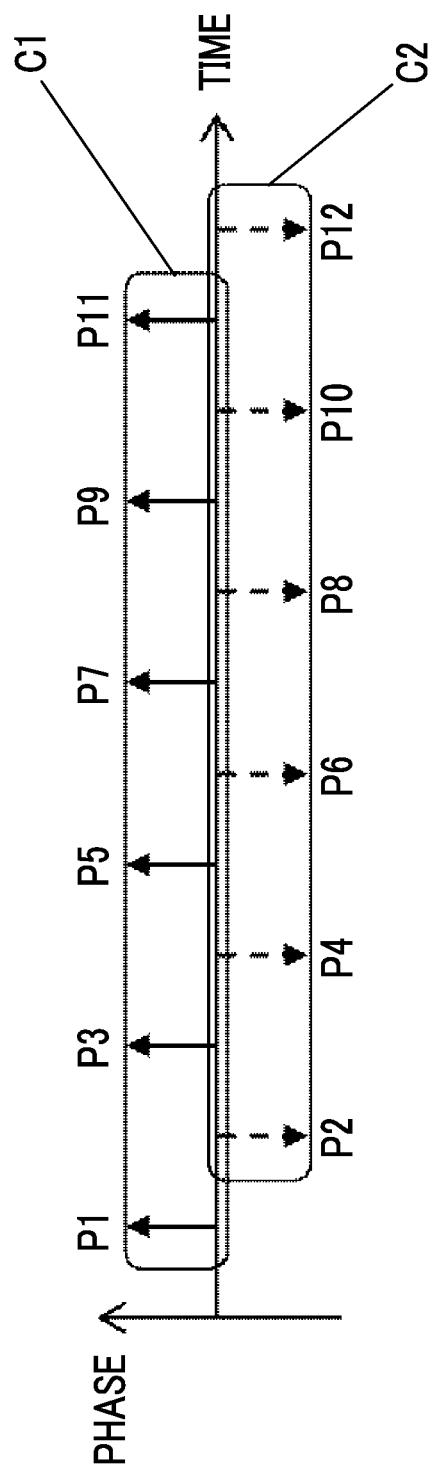
FIG. 7 is a diagram schematically showing IQ signal strings corresponding to the first ultrasonic pulse and the second ultrasonic pulse.

The IQ signal string corresponding to the first ultrasonic pulse FP and the IQ signal string corresponding to the second ultrasonic pulse SP have phases with different polarities. For example, in a case where the first ultrasonic pulse FP has a positive phase and the second ultrasonic pulse SP has a negative phase, as shown in FIG. 7, an IQ signal string C1 including IQ signals P1, P3, P5, P7, P9, and P11 corresponding to the first ultrasonic pulse FP has a positive phase, and an IQ signal string C2 including IQ signals P2, P4, P6, P8, P10, and P12 corresponding to the second ultrasonic pulse SP have a negative phase.

Subsequently, in Step S4, the bubble signal likelihood calculation unit 6 calculates the index representing the bubble signal likelihood using the IQ signal strings C1 and C2 acquired in Step S3. For example, the bubble signal likelihood calculation unit 6 calculates autocorrelation VT based on the IQ signals obtained in Step S3 as shown in Expression (1) described below, calculates power PT of the IQ signals as shown in Expression (2) described below, and calculates a variance value VS as the bubble signal likelihood using the calculated autocorrelation VT and power PT as shown in Expression (3) described below.

$$VT = [\Sigma(P_{j+1} \cdot P^*_j)]/(2n-1) = 1, 2, \ldots, 2n-1) \quad (1)$$

$$PT = (\Sigma |P_k|^2)/(2n)(k = 1, 2, \ldots, 2n) \quad (2)$$

$$VS = 1 - (|VT|/PT) \quad (3)$$

Here, n in Expressions (1) and (2) is a natural number. The autocorrelation of the IQ signals is computed by a product of a later IQ signal in time series and a complex conjugate of an earlier IQ signal in time series between two different IQ signals in time series.

It is desirable that an index value of the bubble signal likelihood is a value normalized without depending on the magnitude of a signal. Although a normalization method is not particularly limited, here, as the simplest method, |VT| is divided by PT, and the index value is normalized such that the index value of the bubble signal likelihood has a value in a range of 0 to 1. In regards to examples of other index values described below, normalization is performed based on the same idea.

A reason that the variance value VS calculated in this way can be used as the index value representing the bubble signal likelihood will be described.

Figure 8:
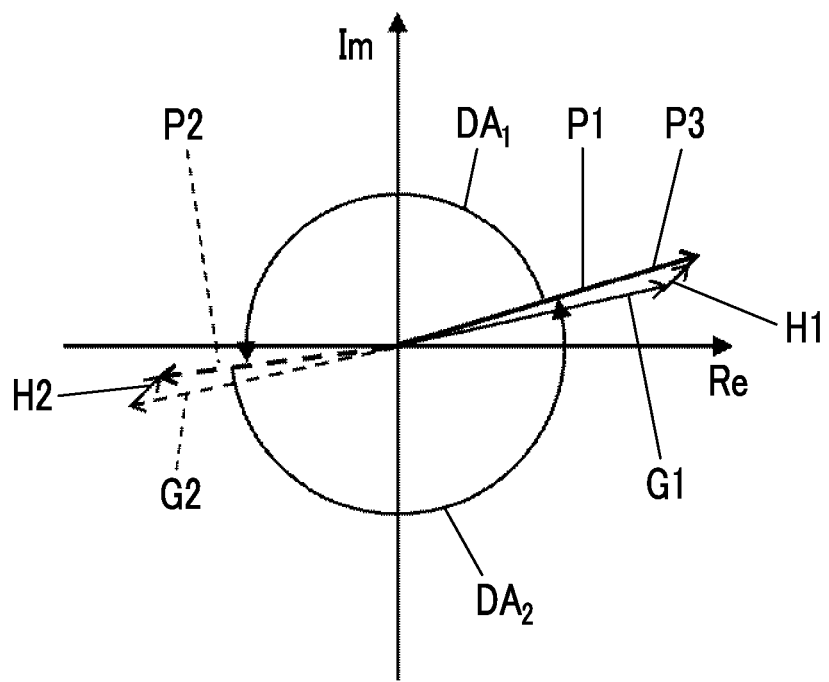
FIG. 8 is a diagram schematically showing an example of IQ signals in a case where contribution of a nonlinear component is comparatively small.

First, in the IQ signal strings C1 and C2 obtained in Step S3, in a case where the influence of the nonlinear signal including the secondary harmonic signal E2 and the bubble signal E3 due to the bubbles of the contrast medium shown in FIGS. 3 and 4 is comparatively small, and the fundamental signals E1 and E4 are dominant, the IQ signal strings C1 and C2 are composed of, for example, the IQ signals shown in FIG. 8. Here, in FIG. 8, IQ signals in a case where there is no influence of the bubbles of the contrast medium in the ultrasound echo, and a component due to the tissue of the subject is dominant, and three IQ signals P1, P2, and P3 are shown as an example of the IQ signals. Actually, although the IQ signals P1 and P3 are signals that are different in magnitude and phase from each other, for description, it is assumed that the IQ signals P1 and P3 are equal to each other.

As shown in FIG. 8, the IQ signals P1 and P3 are represented by, for example, a sum of a fundamental vector G1 corresponding to the fundamental signal E1 and a nonlinear signal vector H1 corresponding to a higher-order harmonic signal, such as the secondary harmonic signal E2 due to the tissue of the subject, and the IQ signal P2 is represented by a sum of a fundamental vector G2 corresponding to the fundamental signal E4 and a nonlinear signal vector H2 corresponding to a higher-order harmonic signal. Here, the signal intensity of the higher-order harmonic signal is extremely small, for example, an order of ⅟10 or less with respect to the signal intensity of the fundamental signal E1, and the magnitude of the nonlinear signal vectors H1 and H2 is extremely small than the magnitude of the fundamental vectors G1 and G2.

For this reason, the IQ signals P1 and P3 are substantially equal to the fundamental vector G1, and the IQ signal P2 is substantially equal to the fundamental vector G2. In this way, in a case where the fundamental signals E1 and E4 are dominant in the IQ signal strings C1 and C2 acquired in Step S3, the randomness of the IQ signal strings C1 and C2 is low. In this case, in regards to the IQ signals P1 and P3, a phase difference $DA_1$ obtained by subtracting the phase of the IQ signal P1 from the phase of the IQ signal P2, and a phase difference $DA_2$ obtained by subtracting the phase of the IQ signal P2 from the phase of the IQ signal P3 substantially become values near 180 degrees.

Figure 9:
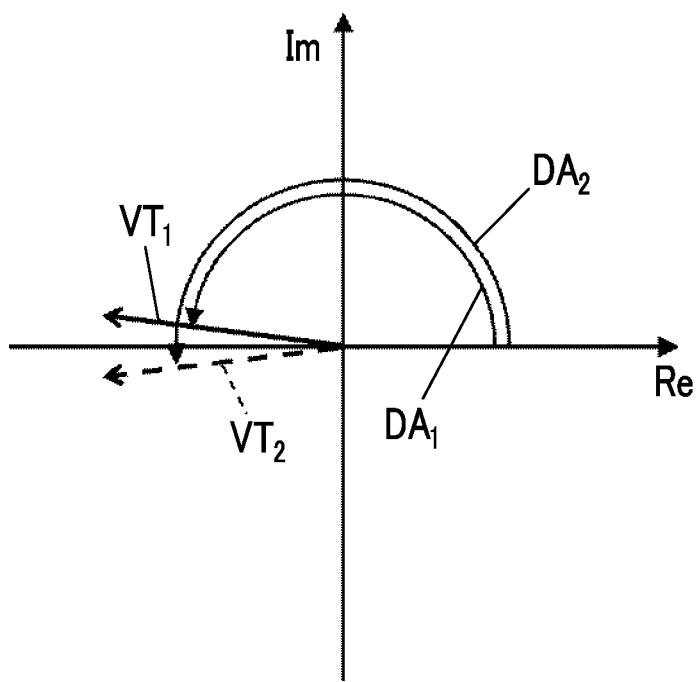
FIG. 9 is a diagram schematically showing an example of a velocity vector in a case where contribution of a nonlinear component is comparatively small.

For this reason, for example, as shown in Expression (4) described below, in a case where autocorrelation between IQ signals adjacent in time series in Expression (1) is set to an autocorrelation vector $VT_j$, the autocorrelation vector $VT_j$ substantially becomes a vector extending toward one direction as shown in FIG. 9. Here, in FIG. 9, the autocorrelation vector $VT_1$ calculated based on the IQ signals P1 and P2 and an autocorrelation vector $VT_2$ calculated based on the IQ signals P2 and P3 are shown, and the autocorrelation vectors $VT_1$ and $VT_2$ have phases $DA_1$ and $DA_2$ near 180 degrees, respectively.

$$VT_j = P_{j+1} \cdot P^*_j (j=1, 2, \ldots, 2n-1) \quad (4)$$

In such a case, since the ratio of an absolute value of the autocorrelation VT shown in Expression (1) to an absolute value of the power PT shown in Expression (2) substantially becomes equal to one, and a variance VS shown in Expression (3) becomes a value near zero.

Figure 10:
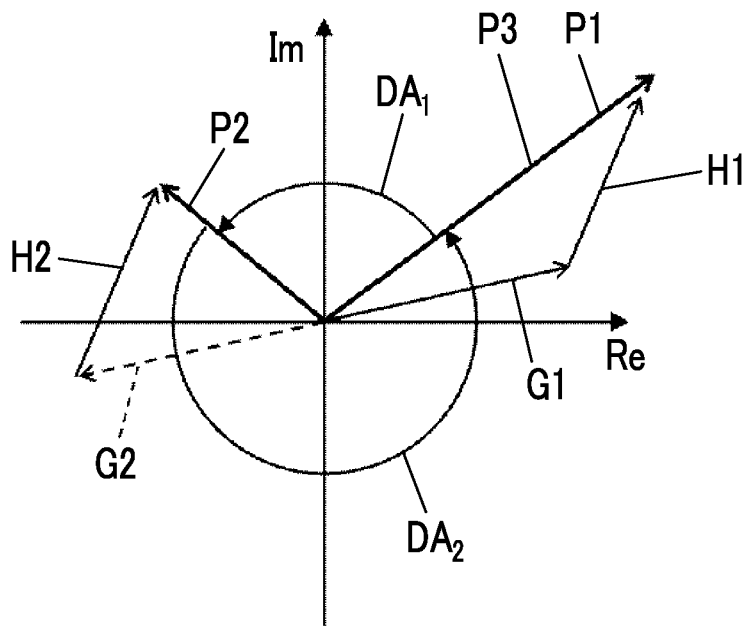
FIG. 10 is a diagram schematically showing an example of IQ signals in a case where contribution of a nonlinear component is comparatively large.

Next, in the IQ signal strings C1 and C2 obtained in Step S3, in a case where the influence of the bubble signal E3 having the nonlinear signal due to the bubbles of the contrast medium is comparatively large, the IQ signal strings C1 and C2 have, for example, IQ signals shown in FIG. 10. Here, the signal intensity of the bubble signal E3 due to the bubbles of the contrast medium is comparatively stronger than the signal intensity of the secondary harmonic signal E2 due to the tissue. For this reason, as quadrature detection is performed in the range FB shown in FIGS. 3 and 4, for example, IQ signals that includes the bubble signal E3 having signal intensity similar to or equal to or higher than the signal intensity of the fundamental signal E1 and the secondary harmonic signal E2 are obtained. As an example of such an IQ signal, the IQ signals P1, P2, and P3 are shown in FIG. 10. As in FIG. 8, actually, although the IQ signals P1 and P3 are signals that are different in magnitude and phase from each other, for description, it is assumed that the IQ signals P1 and P3 are equal to each other.

As shown in FIG. 10, the IQ signals P1 and P3 are represented by the sum of the fundamental vector G1 corresponding to the fundamental signal E1 and the nonlinear signal vector H1 corresponding to the nonlinear signal including the secondary harmonic signal E2 and the bubble signal E3, and the IQ signal P2 is represented by the sum of the fundamental vector G2 corresponding to the fundamental signal E4 and the nonlinear signal vector H2 corresponding to the nonlinear signal including the secondary harmonic signal E2 and the bubble signal E3. In the example shown in FIG. 10, the ratio of the magnitude of the fundamental vector G1 to the magnitude of the nonlinear signal vector H1 and the ratio of the magnitude of the fundamental vector G2 to the magnitude of the nonlinear signal vector H2 are substantially equal to one.

In such a case, the IQ signals P1 and P3 are signals largely deviated from the fundamental vector G1, and the IQ signal P2 is a signal largely deviated from the fundamental vector G2. In this way, in a case where the fundamental signals E1 and E4 are not dominant in the IQ signal strings C1 and C2 acquired in Step S3, and the nonlinear signal is comparatively large, the randomness of the IQ signal is high. In this case, the phase difference $DA_1$ obtained by subtracting the phase of the IQ signal P1 from the phase of the IQ signal P2 and the phase difference $DA_2$ obtained by subtracting the phase of the IQ signal P1 from the phase of the IQ signal P3 becomes, for example, values apart from 180 degrees, such as values near 90 degrees or values near 270 degrees.

Figure 11:
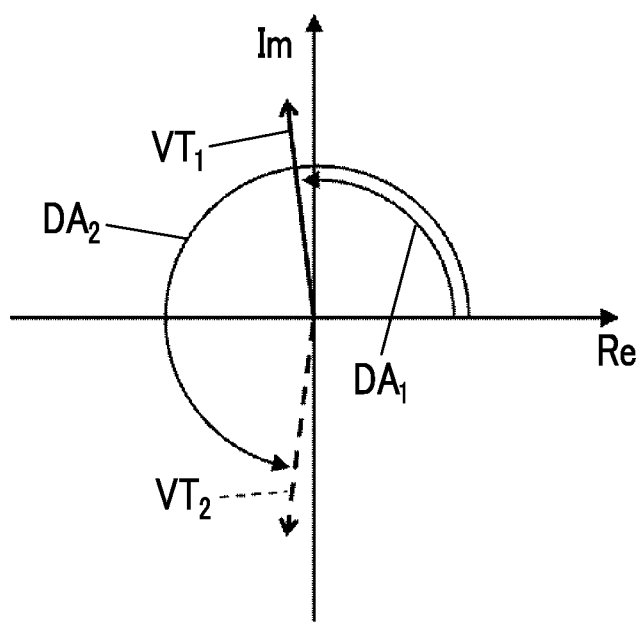
FIG. 11 is a diagram schematically showing an example of a velocity vector in a case where contribution of a nonlinear component is comparatively large.

For this reason, the autocorrelation vector $VT_j$ shown in Expression (4) substantially becomes a vector extending toward an opposite direction, for example, as shown in FIG. 11. Here, in FIG. 11, the autocorrelation vector $VT_1$ calculated based on the IQ signals P1 and P2 and the autocorrelation vector $VT_2$ calculated based on the IQ signals P2 and P3 are shown, the autocorrelation vector $VT_1$ has a phase near 90 degrees, and the autocorrelation vector $VT_2$ has a phase near 270 degrees.

In such a case, in the computation of the autocorrelation VT shown in Expression (1), since the autocorrelation vector $VT_j$ shown in Expression (4) is substantially cancelled, the variance VS shown in Expression (3) becomes a value near one.

Accordingly, as the value of the variance VS is closer to one, the randomness of the IQ signal strings C1 and C2 acquired in Step S3 becomes higher, that is, the influence of the bubble signal E3 due to the bubbles of the contrast medium becomes greater in the IQ signal strings C1 and C2. For this reason, it is understood that the IQ signal strings C1 and C2 are likely to be signals due to the bubbles of the contrast medium. As the value of the variance VS is closer to zero, the randomness of the IQ signal strings C1 and C2 becomes lower, that is, the influence of the bubble signal E3 due to the bubbles of the contrast medium becomes greater in the IQ signal strings C1 and C2, and the influence of the fundamental signals E1 and E4 becomes greater. For this reason, it is understood that the IQ signal strings C1 and C2 are likely to be signals due to the tissue of the subject.

Here, the autocorrelation VT is obtained by the product of one IQ signal of a pair of IQ signals temporally adjacent to each other and a complex conjugate of the other IQ signal; however, in a case where the signal intensity of the bubble signal E3 included in the IQ signals is similar to or equal to or higher than the signal intensity of the fundamental signal E1 and the secondary harmonic signal E2, in the computation of the product, a first IQ signal corresponding to the ultrasound echo from the first ultrasonic pulse FP and a second IQ signal corresponding to the ultrasound echo from the second ultrasonic pulse SP as complex conjugates are alternately replaced, whereby a property that phase differences $DA_j$ to be calculated have values alternately apart from 180 degrees is obtained. In such a case, that is, in calculating the autocorrelation VT, in a case where the order of the first IQ signal and the second IQ signal of which the product is computed are cyclically replaced, the same property is obtained. For this reason, even with autocorrelation that is calculated from IQ signals $P_{j+3}$ and $P_j$, $P_{j+5}$ and $P_j$, or the like, it is possible to obtain the same result.

In this way, in a case where the bubble signal likelihood is calculated in Step S4, in subsequent Step S5, the pulse inversion addition unit 7 acquires the added signals with the fundamental signals E1 and E4 eliminated by adding the IQ signals corresponding to the first ultrasonic pulse FP and the IQ signals corresponding to the second ultrasonic pulse SP using the IQ signal strings C1 and C2 acquired in Step S3.

Figure 12:
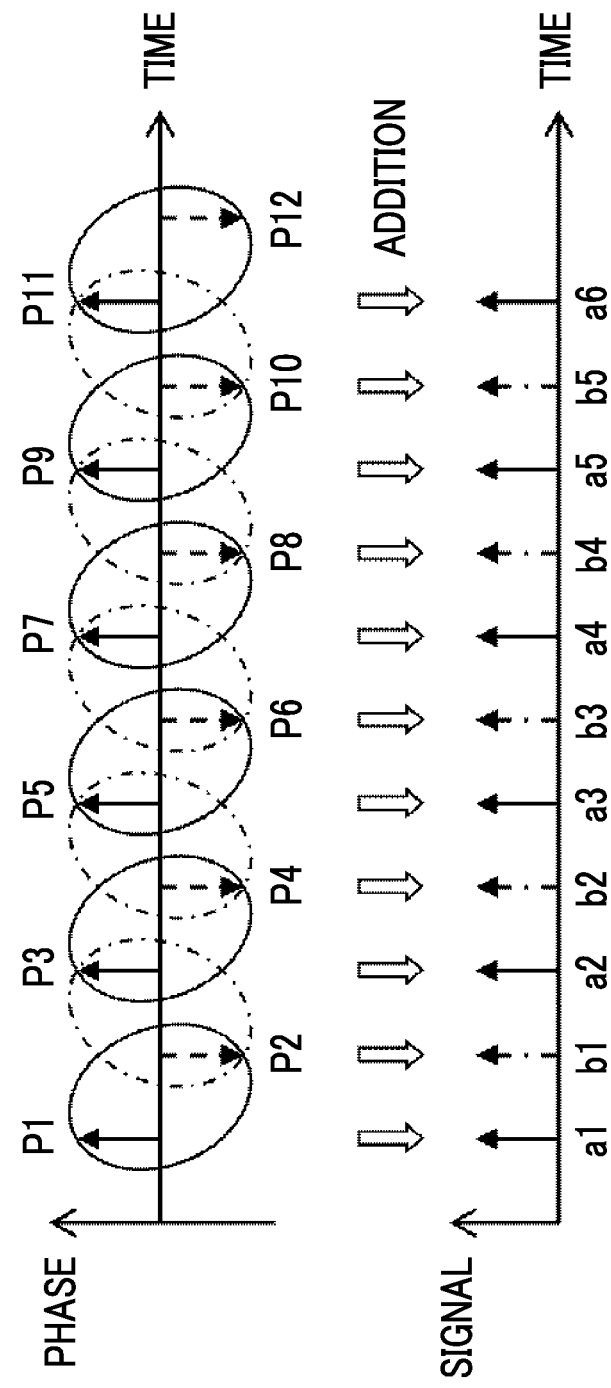
FIG. 12 is a diagram schematically showing a manner of adding the IQ signal string corresponding to the first ultrasonic pulse and the IQ signal string corresponding to the second ultrasonic pulse to calculate an added signal.

For example, as shown in FIG. 12, the pulse inversion addition unit 7 calculates added signals $a_1$, $a_2$, $a_3$, $a_4$, $a_5$, and $a_6$ and $b_1$, $b_2$, $b_3$, $b_4$, and $b_5$ by adding the IQ signals adjacent to one another in time series and different in polarity. In this case, for example, the pulse inversion addition unit 7 calculates the added signals $a_1$, $a_2$, $a_3$, $a_4$, $a_5$, and $a_6$ using Expression (5) described below, and calculates the added signals $b_1$, $b_2$, $b_3$, $b_4$, and $b_5$ using Expression (6) described below.

$$a_m = P_{2m-1} + P_{2m} (m=1,2,\ldots,n) \quad (5)$$

$$b_q = P_{2q} + P_{2q+1} (q=1,2,\ldots,n-1) \quad (6)$$

In subsequent Step S6, the nonlinear signal information calculation unit 8 calculates at least one of the power or the velocity vector of the nonlinear signal including the secondary harmonic signal E2 due to the tissue of the subject and the bubble signal E3 having the nonlinear signal due to the bubbles of the contrast medium introduced into the subject using the added signals $a_m$ and $b_q$ calculated in Step S5. For example, the nonlinear signal information calculation unit 8 can calculate power PB of the bubble signal E3 using Expression (7) described below, and can calculate a velocity of VB of the bubble signal E3 using Expression (8) described below.

$$PB = [\Sigma |a_m|^2 + \Sigma |b_q|^2]/(2n-1)$$

$$(m=1,2,\ldots,n, q=1,2,\ldots,n-1) \quad (7)$$

$$VB = [E(a_{r+1} \cdot a^*_r) + \Sigma(b_{t+1} \cdot b^*_t)]/(2n-3)$$

$$(r=1,2,\ldots,n-2, t=1,2,\ldots,n-3) \quad (8)$$

Figure 13:
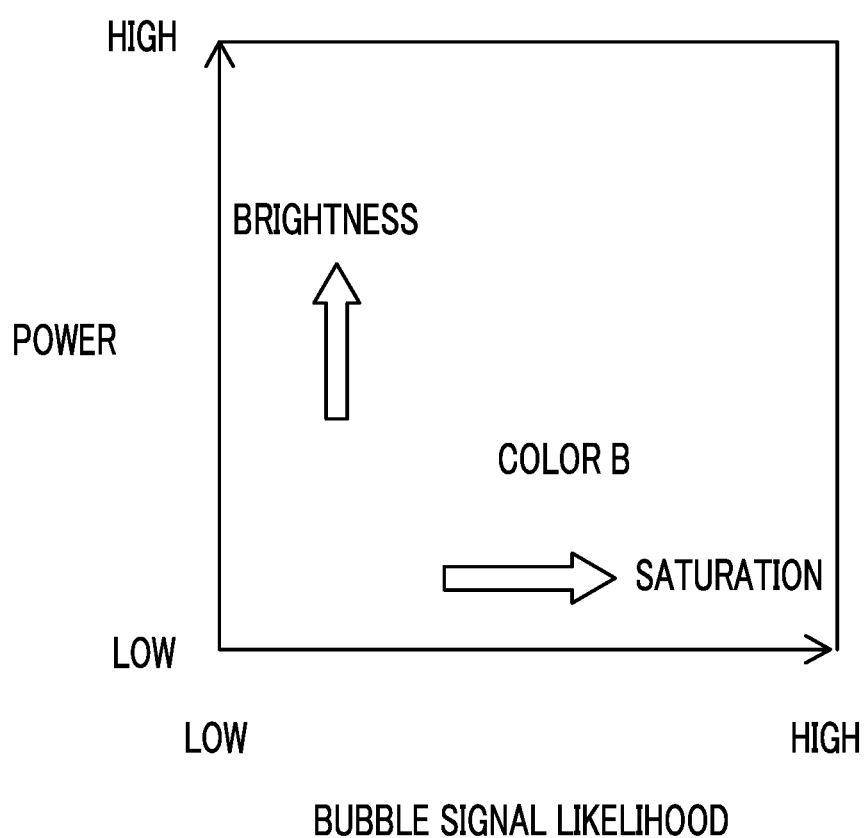
FIG. 13 is a diagram schematically showing a display example of power and a bubble signal likelihood obtained by the ultrasound diagnostic apparatus according to the embodiment of the invention.

In subsequent Step S7, the image generation unit 9 generates the ultrasound image based on at least one of the power PB or the velocity VB of the nonlinear signal calculated in Step S6 and the bubble signal likelihood calculated in Step S4 and displays the generated ultrasound image on the display unit 11. For example, as shown in FIG. 13, the image generation unit 9 can generate an ultrasound image by a so-called color map in which a value of the power PB of the nonlinear signal calculated in Step S6 is represented by a change in brightness and the index value of the bubble signal likelihood is represented by a change in saturation of a color B, and can display the generated ultrasound image on the display unit 11. In the example shown in FIG. 13, the greater the value of the power PB is, the greater the brightness is, and the greater the index value of the bubble signal likelihood is, the higher the saturation of the color B is.

In this way, the operation of the ultrasound diagnostic apparatus 1 according to the embodiment of the invention ends.

As above, with the ultrasound diagnostic apparatus 1 according to the embodiment of the invention, since the bubble signal likelihood calculation unit 6 calculates the bubble signal likelihood based on the autocorrelation VT obtained from the IQ signal strings C1 and C2 acquired by the quadrature detection unit 5, it is possible to distinguish a signal due to the tissue of the subject and a signal due to the bubbles of the contrast medium introduced into the subject easily and in a short time.

Since the ultrasound image is generated based on the calculated index value of the bubble signal likelihood and at least one of the power PB or the velocity VB of the nonlinear signal, and the ultrasound image is displayed on the display unit 11, it is possible to allow the user to easily ascertain the signal due to the bubbles of the contrast medium introduced into the subject.

In the embodiment, although the bubble signal likelihood calculation unit 6 calculates the variance VS shown in Expression (3) as the index value of the bubble signal likelihood, the index value is not limited thereto insofar as the index value is calculated using the autocorrelation VT calculated based on the IQ signal strings. For example, as shown in Expression (9) described below, the bubble signal likelihood calculation unit 6 can calculate a variance value VX as a bubble signal likelihood by computing the variance value VX using $|VT|/PT$ in Expression (3). In this case, as the variance value VX is closer to one, determination can be made that the IQ signal strings C1 and C2 acquired by the quadrature detection unit 5 are likely to be signals due to the tissue of the subject, and as the variance value VX is closer to zero, determination can be made that the IQ signal strings C1 and C2 are likely to be signals due to the bubbles of the contrast medium.

$$VX = |VT|/PT \quad (9)$$

For example, the bubble signal likelihood calculation unit 6 may calculate a variance value of a phase difference of IQ signals adjacent to each other in time series in the IQ signal strings C1 and C2 acquired by the quadrature detection unit 5 as the bubble signal likelihood. For example, as shown in Expression (10) described below, in a case where a real part of an IQ signal $P_k$ is $X_k$, and an imaginary part of the IQ signal $P_k$ is $Y_k$, a phase difference $DA_j$ of IQ signals adjacent to each other in time series is represented by Expression (11) described below. Here, i in Expression (10) described below represents an imaginary unit.

$$P_k = X_k + iY_k (k=1,2,\ldots,2n) \quad (10)$$

$$DA_j = \tan^{-1}[(Y_{j+1}X_j - X_{j+1}Y_j)/(X_{j+1}X_j + Y_{j+1}Y_j)](j=1,2,\ldots,2n-1) \quad (11)$$

As shown in Expression (12) described below, the bubble signal likelihood calculation unit 6 can calculate a variance value VS1 of the phase difference $DA_j$ calculated by Expression (11) as the index value of the bubble signal likelihood. Here, $E(DA_j)$ in Expression (12) described below is an arithmetical mean of the phase difference $DA_3$. As shown in FIG. 9, in a case where the influence of the bubble signal E3 having the nonlinear signal is small, $DA_j$ substantially becomes identical. For this reason, VS1 is close to zero. On the other hand, as shown in FIG. 11, in a case where the influence of the bubble signal E3 having the nonlinear signal is large, $DA_3$ and $DA_{j+1}$ become values apart from each other. For this reason, VS1 becomes a value greater significantly than zero. Therefore, as the variance value VS1 is closer to one, determination can be made that the IQ signal strings C1 and C2 acquired by the quadrature detection unit 5 are likely to be signals due to the bubbles of the contrast medium, and as the variance value VS1 closer to zero, determination can be made that the IQ signal strings C1 and C2 are likely to be signals due to the tissue of the subject. With the same idea as the autocorrelation VT, it is possible to obtain the same result even with the phase difference calculated from $P_{j+3}$ and $P_j$, $P_{j+5}$ and $P_j$, or the like.

$$VS1=1-[\Sigma(DA_j)^2/\{\Sigma DA_j^2/(2n-1)\}](j=1,2,\ldots,2n-1) \quad (12)$$

For example, as shown in Expression (13) described below, the bubble signal likelihood calculation unit 6 may calculate a variance value VX1 in Expression (12) as the bubble signal likelihood. In this case, as the variance value VX1 is closer to one, determination can be made that the IQ signal strings C1 and C2 acquired by the quadrature detection unit 5 are likely to be signals due to the tissue of the subject, and as the variance value VX1 is closer to zero, determination can be made that the IQ signal strings C1 and C2 are likely to be signals due to the bubbles of the contrast medium.

$$VX1=[E(DA_j)^2/\{\Sigma DA_j^2/(2n-1)\}](j=1,2,\ldots,2n-1) \quad (13)$$

For example, as shown in Expression (14) described below, the bubble signal likelihood calculation unit 6 may calculate a variance value VS2 of amplitude of the IQ signal strings C1 and C2 acquired by the quadrature detection unit 5 as the index value of the bubble signal likelihood. Here, $E(|P_k|)$ in Expression (14) described below is an arithmetic mean of an absolute value, that is, amplitude of the IQ signal $P_k$. As shown in FIG. 8, in a case where the influence of the bubble signal E3 having the nonlinear signal is small, $|P_k|$ substantially becomes identical. For this reason, VS2 is close to zero. On the other hand, as shown in FIG. 10, in a case where the influence of the bubble signal E3 having the nonlinear signal is large, $|P_k|$ and $|P_{k+1}|$ become values apart from each other. For this reason, VS2 becomes a value significantly greater than zero. Therefore, as the variance value VS2 is closer to one, determination can be made that the IQ signal strings C1 and C2 acquired by the quadrature detection unit 5 are likely to be signals due to the bubbles of the contrast medium, and as the variance value VS2 is closer to zero, determination can be made that the IQ signal strings C1 and C2 are likely to be signals due to the tissue of the subject.

$$VS2=1-[E(|P_k|)^2/\{\Sigma|P_k|^2/(2n-1)\}](k=1,2,\ldots,2n) \quad (14)$$

For example, as shown in Expression (15) described below, the bubble signal likelihood calculation unit 6 may calculate a variance value VX2 in Expression (14) as the index value of the bubble signal likelihood. In this case, as the variance value VX2 is closer to one, determination can be made that the IQ signal strings C1 and C2 acquired by the quadrature detection unit 5 are likely to be signals due to the tissue of the subject, and as the variance value VX2 is closer to zero, determination can be made that the IQ signal strings C1 and C2 are likely to be signals due to the bubbles of the contrast medium.

$$VX2=[E(|P_k|)^2/\{\Sigma|P_k|^2/(2n-1)\}](k=1,2,\ldots,2n) \quad (15)$$

As a display example of the ultrasound image generated by the image generation unit 9 in the embodiment, although the ultrasound image shown in FIG. 13 based on the value of the power PB of the bubble signal E3 and the bubble signal likelihood is shown, the ultrasound image generated by the image generation unit 9 is not limited thereto. For example, in the display example of the ultrasound image shown in FIG. 13, the image generation unit 9 displays only a place where the index value of the bubble signal likelihood is greater than a given value using a color B, and does not display a place where the index value of the bubble signal likelihood is smaller than the given value using the color B, whereby it is possible to display the value of the power PB on a gray scale.

Figure 14:
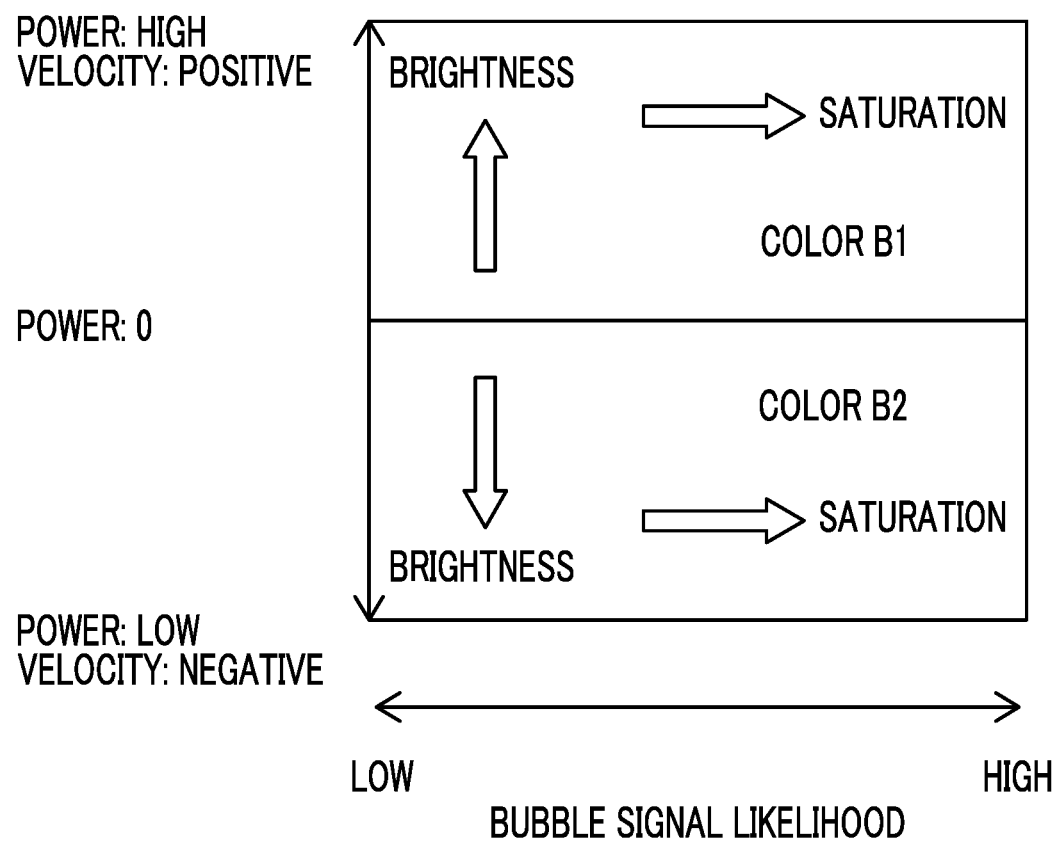
FIG. 14 is a diagram schematically showing a display example of power, a velocity, and a bubble signal likelihood obtained by the ultrasound diagnostic apparatus according to the embodiment of the invention.

For example, as shown in FIG. 14, the image generation unit 9 can select one of a color B1 and a color B2 according to the polarity of the phase of the velocity VB of the nonlinear signal including the secondary harmonic signal E2 due to the tissue of the subject and the bubble signal E3 having the nonlinear signal due to the bubbles of the contrast medium introduced into the subject, can generate an ultrasound image in which the value of the power PB is represented by a change in brightness and the index value of the bubble signal likelihood is represented by a change in saturation of the color B1 and the color B2, and can display the generated ultrasound image on the display unit 11. In the example shown in FIG. 14, the greater the value of the power PB is, the greater the brightness is, in a region where the phase of the velocity VB is positive, the greater the index value of the bubble signal likelihood is, the higher the saturation of the color B1 is, and in a region where the phase of the velocity VB is negative, the greater the index value of the bubble signal likelihood is, the higher the saturation of the color B2 is.

For example, the image generation unit 9 may generate an ultrasound image based on the value of the phase of the velocity VB of the nonlinear signal and the index value of the bubble signal likelihood, and may display the generated ultrasound image on the display unit 11. For example, in this case, as in the example shown in FIG. 14, the image generation unit 9 can select one of the color B1 and the color B2 according to the polarity of the phase of the velocity VB, and can generate an ultrasound image in which an absolute value of the phase of the velocity VB is represented by a change in brightness, and the index value of the bubble signal likelihood is represented by a change in saturation of the color B1 and the color B2.

The image generation unit 9 may generate an ultrasound image based on at least one of the power PB or the velocity VB of the nonlinear signal, and may display the generated ultrasound image on the display unit 11. For example, though not shown, the image generation unit 9 can generate an ultrasound image on a gray scale such that the greater the power PB is, the greater the brightness is.

In a case of generating the ultrasound image based on at least one of the power PB or the velocity VB of the nonlinear signal, the image generation unit 9 can display the index value of the bubble signal likelihood on the display unit 11 to be superimposed on or in parallel with the ultrasound image. In this case, for example, though not shown, the image generation unit 9 can display an index value of a bubble signal likelihood corresponding to a position on the ultrasound image designated by the user through the operating unit 14 on the display unit 11. In this case, for example, a cursor that can be operated by the user through the operating unit 14 can be displayed on the display unit 11, and the user can designate a position on the ultrasound image through the operating unit 14.

A display different from the display unit 11 may be provided in the ultrasound diagnostic apparatus 1, and the index value of the bubble signal likelihood may be displayed on the display.

Though not shown, a B mode processing unit that generates a B mode image is provided in the ultrasound diagnostic apparatus 1, whereby the power PB and the velocity VB of the nonlinear signal and the bubble signal likelihood can be imaged and displayed on the display unit 11 in such a manner as to be superimposed on the B mode image representing a tomographic image of the subject. The power PB and the velocity VB of the nonlinear signal and the bubble signal likelihood may be imaged and displayed on the display unit 11 in parallel with the B mode image representing the tomographic image of the subject.

In the embodiment, the pulse inversion addition unit 7 adds the IQ signals corresponding to the first ultrasonic pulse FP and the IQ signals corresponding to the second ultrasonic pulse SP adjacent in time series, the IQ signals corresponding to the first ultrasonic pulse FP and the IQ signals corresponding to the second ultrasonic pulse SP may be added in any combination not adjacent in time series. However, it is preferable that the IQ signals corresponding to the first ultrasonic pulse FP and the IQ signals corresponding to the second ultrasonic pulse SP adjacent in time series are added because the influence of the motion of the tissue of the subject is reduced.

Although the pulse inversion addition unit 7 calculates the added signal $a_m$ using Expression (5) and calculates the added signal $b_q$ using Expression (6), the pulse inversion addition unit 7 may calculate only one of the added signals $a_m$ and $b_q$.

EXPLANATION OF REFERENCES

1: ultrasound diagnostic apparatus,
2: transducer array,
3: transmission unit,
4: reception unit,
5: quadrature detection unit,
6: bubble signal likelihood calculation unit,
7: pulse inversion addition unit,
8: nonlinear signal information calculation unit,
9: image generation unit,
10: display controller,
11: display unit,
12: apparatus controller,
13: storage unit,
14: operating unit,
15: processor,
16: amplification unit,
17: AD conversion unit,
18: beamformer,
a1, a2, a3, a4, a5, a6, b1, b2, b3, b4, b5: added signal,
B, B1, B2: color,
C1, C2: IQ signal string,
$DA_1$, $DA_2$: phase difference,
E1, E4: fundamental signal,
E2: secondary harmonic signal,
E3: bubble signal,
FB: range,
FP: first ultrasonic pulse,
G1, G2: fundamental vector,
H1, H2: nonlinear signal vector,
$VT_1$, $VT_2$: autocorrelation vector,
L1, L2, L3, L4, L5: scanning line,
P1, P2, P3, P4, P5, P6, P7, P8, P9, P10, P11, P12: IQ signal,
PRT1: time interval,
SP: second ultrasonic pulse.

What is claimed is:

1. An ultrasound diagnostic apparatus comprising:
a transducer array; and
a processor configured to
transmit a set of a first ultrasonic pulse and a second ultrasonic pulse having phases inverted from each other on the same scanning line from the transducer array into a subject N times equal to or greater than at least two times,
acquire reception signals based on a signal output from the transducer array received an ultrasound echo generated in the subject, based on the set of the first ultrasonic pulse and the second ultrasonic pulse transmitted N times,
convert the reception signals to IQ signals by performing quadrature detection in a determined range on the reception signals which are acquired, to acquire an IQ signal string corresponding to the first ultrasonic pulse transmitted N times from the transducer array and an IQ signal string corresponding to the second ultrasonic pulse transmitted N times from the transducer array,
acquire image signals with a fundamental component eliminated by adding IQ signals corresponding to the first ultrasonic pulse and IQ signals corresponding to the second ultrasonic pulse using the IQ signal strings,
calculate at least one of an autocorrelation, a variance value of a phase difference or a variance value of an amplitude as index values of a bubble signal likelihood representing a probability of a bubble of a contrast medium, based on the IQ signal strings corresponding to the reception signals which are acquired, and
generate an ultrasound image based on the index values of the bubble signal likelihood which are calculated and the image signals which are acquired, where the index values of the bubble signal likelihood are mapped at corresponding positions on the ultrasound image and are represented by saturations of a color according to a magnitude of the index values of the bubble signal likelihood.

2. The ultrasound diagnostic apparatus according to claim 1,
wherein the processor is further configured to calculate at least one of power or a velocity of a nonlinear signal from the image signals.

3. The ultrasound diagnostic apparatus according to claim 2,
wherein the processor is further configured to generate the ultrasound image based on at least one of the power or the velocity of the nonlinear signal.

4. The ultrasound diagnostic apparatus according to claim 3,
wherein the processor is further configured to generate the ultrasound image according to a color map based on at least one of the power or the velocity of the nonlinear signal and the bubble signal likelihood.

5. The ultrasound diagnostic apparatus according to claim 1, further comprising:
a display monitor configured to display the ultrasound image.

6. A method of controlling an ultrasound diagnostic apparatus, the method comprising:
- transmitting a set of a first ultrasonic pulse and a second ultrasonic pulse having phases inverted from each other on the same scanning line from a transducer array into a subject N times equal to or greater than at least two times;
- acquiring reception signals based on a signal output from the transducer array received an ultrasound echo generated in the subject, based on the set of the first ultrasonic pulse and the second ultrasonic pulse transmitted N times;
- converting the reception signals to IQ signals by performing quadrature detection in a determined range on the reception signals which are acquired, to acquire an IQ signal string corresponding to the first ultrasonic pulse transmitted N times from the transducer array and an IQ signal string corresponding to the second ultrasonic pulse transmitted N times from the transducer array;
- acquiring image signals with a fundamental component eliminated by adding IQ signals corresponding to the first ultrasonic pulse and IQ signals corresponding to the second ultrasonic pulse using the acquired IQ signal strings;
- calculating at least one of an autocorrelation, a variance value of a phase difference or a variance value of an amplitude as index values of a bubble signal likelihood representing a probability of a bubble of a contrast medium, based on the acquired IQ signal strings corresponding to the reception signals which are acquired; and
- generating an ultrasound image based on the index values of the bubble signal likelihood which are calculated and the image signals which are acquired, where the index values of the bubble signal likelihood are mapped at corresponding positions on the ultrasound image and are represented by saturations of a color according to a magnitude of the index values of the bubble signal likelihood.

* * * * *